US011285229B2

(12) United States Patent
Preminger et al.

(10) Patent No.: US 11,285,229 B2
(45) Date of Patent: Mar. 29, 2022

(54) APPARATUS AND SYSTEM FOR STERILIZATION OF GARMENTS USING ULTRAVIOLET LIGHT

(71) Applicant: SteriLux Systems, LLC, New York, NY (US)

(72) Inventors: Jonathan Preminger, New York, NY (US); Jason Lansdown, New York, NY (US)

(73) Assignee: SteriLux Systems, LLC, New York, NY (US)

( * ) Notice: Subject to any disclaimer, the term of this patent is extended or adjusted under 35 U.S.C. 154(b) by 138 days.

(21) Appl. No.: 16/122,029

(22) Filed: Sep. 5, 2018

(65) Prior Publication Data

US 2019/0070325 A1      Mar. 7, 2019

Related U.S. Application Data

(60) Provisional application No. 62/570,225, filed on Oct. 10, 2017, provisional application No. 62/555,172, filed on Sep. 7, 2017.

(51) Int. Cl.
*A61L 2/10* (2006.01)
*A41D 13/002* (2006.01)

(52) U.S. Cl.
CPC .............. *A61L 2/10* (2013.01); *A41D 13/002* (2013.01); *A61L 2202/11* (2013.01);
(Continued)

(58) Field of Classification Search
CPC .... A61L 2/10; A61L 2202/12; A61L 2202/26; A61L 2202/11; A61L 2209/111; A61L 2202/14; A41D 13/002
See application file for complete search history.

(56) References Cited

U.S. PATENT DOCUMENTS 9,107,973 B1 *   8/2015   Robinson .................. A61L 2/22
2008/0213129 A1 * 9/2008   van der Pol .............. A61L 2/10
                                                                   422/24
(Continued)

FOREIGN PATENT DOCUMENTS

KR       20110006814 U  *  7/2011   .............. A61L 2/10
KR       20120122519 A  * 11/2012
(Continued)

OTHER PUBLICATIONS

Translation of Jang (Year: 2011).*
(Continued)

*Primary Examiner* — Sean E Conley
*Assistant Examiner* — Brendan A Hensel
(74) *Attorney, Agent, or Firm* — Nixon Peabody LLP

(57) ABSTRACT

An ultraviolet (UV) sterilization system and a device for sterilizing a garment having shoulder, torso, and sleeve portions including a garment enclosure; a garment hanger; and at least three UV emitter sets, wherein the garment enclosure comprises a housing and a door that are affixed to each other to provide an interior cavity of the garment enclosure, wherein the housing further includes a plurality of housing walls that encapsulate the housing, and wherein each of the plurality of housing walls comprises a housing-wall inside surface located within the plurality of housing walls and a housing-wall outside surface located outside the plurality of housing walls.

18 Claims, 7 Drawing Sheets

(52) U.S. Cl.
CPC ....... *A61L 2202/12* (2013.01); *A61L 2202/14* (2013.01); *A61L 2202/26* (2013.01); *A61L 2209/111* (2013.01)

(56) References Cited

U.S. PATENT DOCUMENTS

| | | | | |
|---|---|---|---|---|
| 2008/0265179 | A1* | 10/2008 | Havens | A61L 2/10 |
| | | | | 250/492.1 |
| 2015/0118107 | A1* | 4/2015 | Sunkara | A61L 2/24 |
| | | | | 422/24 |
| 2016/0093412 | A1* | 3/2016 | Liao | A61L 2/10 |
| | | | | 250/221 |
| 2017/0020321 | A1* | 1/2017 | Jiang | A47G 25/50 |

FOREIGN PATENT DOCUMENTS

KR 20130112556 A * 10/2013
KR 101565953 B1 * 11/2015

OTHER PUBLICATIONS

Translation of Kim (Year: 2015).*
Translation of Ryu (Year: 2012).*
Translation of Yoon (Year: 2013).*
Clothes Hanger—Wikipedia (Year: 2014).*
Toolbox-Training: UV-Facts (Year: 2017).*

* cited by examiner

APPARATUS AND SYSTEM FOR STERILIZATION OF GARMENTS USING ULTRAVIOLET LIGHT

CROSS-REFERENCE TO RELATED APPLICATIONS

This application claims the benefit of and priority under 35 U.S.C. § 119(e) to U.S. provisional patent application Nos. 62/555,172, filed Sep. 7, 2017 and 62/570,225, filed Oct. 10, 2017, the entirety of which is hereby incorporated by reference.

BACKGROUND OF THE PRESENT DISCLOSURE

As a general proposition, light in the ultraviolet region of the electromagnetic spectrum has proven particularly useful in killing bacteria in an array of professional and industrial environments. Moreover, apparatus for sterilizing garments with ultraviolet (UV) light have been conceived and manufactured. Among the extant apparatus is a locker-type enclosure, the interior of which includes one or more UV-light sources and which can accommodate the hanging of garment for selective sterilization by UV light emitted by the one or more light sources.

Against the backdrop of the previous development of UV-light sterilization apparatus, improvements have been made incrementally. Even so, while existing UV-emitting enclosures are capable of sterilizing external garment surfaces within "line of sight" of the UV-emitting sources disposed along the enclosure's interior, such a configuration is insufficient for sterilizing the inside surfaces of garments such as medical and lab coats and shirts. Areas of particular concern that go unsterilized by current UV-sterilization systems are sleeve and pocket interiors. When a garment is hanged in the normal manner, the sleeves hang down to the sides of the portion of the garment designed for the torso and the UV-light simply cannot access the sleeve interiors or the portions of the sleeves and torso portion that are adjacent one another.

One "work-around" the partially addresses the shortcomings of previous UV-sterilization enclosures is to hang a garment on a hanger within the enclosure in the normal manner and send it through a first sterilization cycle. The first cycle will sterilize most of the garment exterior, with the exception of the aforementioned portions of the sleeves and torso portion that hand adjacent one another. Subsequent to such a first cycle, a user can remove the garment from the enclosure and turn it inside out, hang it back on a hanger, and send through a second sterilization cycle, which second cycle will sterilize most of the interior surfaces of the garment.

Two disadvantages of the described work-around are (i) it is a two-stage process requiring more than twice the time required to run a single sterilization cycle and (ii) while it results in a substantially greater percentage of a garment's surface being sterilized than a first sterilization cycle alone, it still does not sterilize all—or even nearly all—of the garment surfaces. Left of sterilized by the two-stage work-around are, again, (i) portions of the sleeves and torso portion that hand adjacent one another, on both the interior and exterior surfaces of the garment and (ii) pocket interiors, pocket interiors representing a garment region that hosts high concentrations of bacteria.

SUMMARY OF THE PRESENT DISCLOSURE

Accordingly, a need exists for a sterilization system that combines elements cooperatively configured to holistically sterilize a garment in a single stage using ultraviolet light.

In each of various illustrative embodiments, a systemic approach to single-stage garment sterilization is achieved by uniquely configured, mutually cooperative elements. More specifically, an illustrative configuration involves three major elements: (i) a garment enclosure, (ii) a uniquely-configured garment hanger, and (iii) a set of "orbs," each of which orbs is configured to selectively emit UV light, and is alternatively referred to as a UV-emitting orb. Each of the three major elements is described in detail below.

In accordance with one implementation, a garment enclosure that allows one-step sterilization using UV light is disclosed. The garment enclosure includes a housing, wherein the housing further includes a plurality of housing walls defining an interior garment cavity configured to selectively receive and temporarily house at least one garment to be sterilized; a door that is selectively openable and closable for introduction and removal of garments from the internal garment cavity; and at least three UV-emitter sets. The door may be configured to be closable to prevent leakage to the housing exterior of UV light during sterilization cycles. The housing may resemble a shape of, e.g., a cabinet, a locker, a closet, an armoire, or any other enclosure.

Each housing wall may include a housing-wall inside and outside surface defining, respectively, a portion of the overall housing interior and exterior. The housing-wall inside faces an interior of the housing wall and a surface, wherein surface may include a first UV-emitter set. The first UV-emitter set may include a UV-emitter configured to selectively emit light within the ultraviolet range of the electromagnetic spectrum when energized by electrical current. The UV-emitter is hereinafter alternatively referred to as a UV-emitter or UV-emitting element. In another embodiment of the present disclosure, a housing including only a single UV-emitter is within the scope of the overall concept, and it is envisioned that the housing interior have disposed along more than one inside wall surface a plurality of UV-emitters configured and mutually arranged to selectively bombard the housing interior with UV light.

Additionally, in order to facilitate the thorough and even distribution of UV light throughout the housing interior, the housing-wall inside surfaces may be configured to be reflective of UV light. In one embodiment of the present disclosure, UV reflectivity is achieved by fabricating the interior of the housing walls from a reflective material. The reflective materials may include, e.g., aluminum, polished aluminum, glass, hydroponics, any material with a greater than 75% reflectivity of UV light, or any combinations thereof. In another embodiment of the present disclosure, the housing-wall inside surfaces may be coated in a UV-reflective coating. The UV-reflective coating may include aluminum, glass, hydroponics, any material with a greater than 75% reflectivity of UV light, or any combinations thereof. In yet another embodiment of the present disclosure, reflective elements may be fastened to the housing-wall inside surfaces by any of various fastening element including, e.g., rivets, threaded fasteners, and an adhesive such as glue or epoxy, or any combinations thereof.

While it is envisioned that various embodiments include a garment enclosure preassembled with the specific sterilization purposes in mind, and therefore incorporating, at the time of manufacture, the UV-emitter and reflective surfaces along the housing-wall inside surfaces, a retrofitting option is also disclosed herein. More specifically, according to an aspect of the present disclosure, a retrofitting kit includes at least one sterilization panel configured for installation into an existing garment enclosure (e.g., locker, cabinet, armoire, and the like). The sterilization panel has depending therefrom, or otherwise incorporated therein, at least one UV emitters. Each panel of the retrofitting kit is configured for mounting on an inner surface (e.g., inside housing wall) of the pre-existing garment enclosure. In another embodiment of the present disclosure, the retrofitted garment enclosure would then function in essentially the same manner as a garment enclosure with UV-emitter that is fabricated as a single unit from inception in accordance with the principles of the present invention.

Whether used in conjunction with a garment enclosure fabricated from inception to emit UV light, or in conjunction with a retrofitted garment enclosure, an overall UV-sterilization system configured in accordance with the present invention further includes a uniquely configured garment hanger. In one embodiment, the garment hanger is configured for hanging a garment includes at least a torso portion with a torso-portion interior, an exterior surfaces, a left and a right sleeve portions depending from the torso portion, sleeve-portion interior, and exterior surfaces. The garment hanger further includes a hook portion by which the hanger may be hung within the garment enclosure. Depending from the hook portion is a garment-support frame, which includes left-side and right side hanger arms corresponding to, and configured to at least partially coextend with, respectively, the left and right sleeve portions of the garment. In order to facilitate UV-sterilization of the torso-portion and sleeve-portion interior surfaces, a second UV-emitter set includes at least one electrically energizable UV-emitter that is carried by the garment support frame of various garment hanger embodiments.

In an embodiment of the present disclosure, the garment enclosure includes a hanger station configured to receive hook portion of the garment hanger. The hook portion may be hanged on the hanger station. The hanger station may include a pole. The presence of the hook portion upon the hanger station defines a detectable registration condition. That is, in such an embodiment, when the hook portion is hung as intended and properly seated upon the hanger station, the garment hanger is regarded as "in registration" with the hanger station. In at least one embodiment, the registration condition of the hanger facilitates selective energizing of the second UV-emitter set from the exterior of the garment housing. This may be facilitated by the proper seating of the hook portion upon the hanger station establishing electrical connectivity between the second UV-emitter set of the garment hanger and a power source that, for example, provides electrical power to the garment enclosure (e.g., to the first UV-emitter set disposed within the housing interior of the garment enclosure). The power source may include, e.g., a battery, an electricity outlet, and the like.

In addition, or as an alternative, to the registration condition enabling electrical energizing of a second UV-emitter set, if present, the registration condition may be tied to the overall functionality of the UV-sterilization system. That is, for example, the system as a whole may not be energizable in some implementations if at least one garment hanger is not detected as "in registration" with at least one hanger station within the garment enclosure.

As described, one of the problems in association with previous UV-sterilization systems is that, when a sleeved garment is hung on a hanger of substantially standard configuration, parts of the torso-portion and sleeve-portion exterior surfaces hang directly adjacent and in contact with one another, thereby preventing impingement thereon by sterilizing ultraviolet light. Various embodiments of the present UV-sterilization system include garment hangers uniquely configured to address this issue.

According to one hanger configuration, each of the left-side and right-side hanger arms comprises a shoulder-support portion and a corresponding sleeve-support portion configured to support, respectively, a shoulder and sleeve portion of a sleeved garment. As one would expect, the sleeve support portion is more distant from the hook portion than is the corresponding shoulder-support portion. Each of the left-side and right-side hanger arms further includes an elbow defining an obtuse angle between the shoulder-support and sleeve-support portions thereof. The elbow is such that the sleeve portion of a garment hanging on the hanger protrudes one of (i) forwardly and (ii) backwardly from the torso portion of the garment in order to maximize the surface area along each sleeve-portion exterior surface that is supported out of contact with the torso-portion exterior surface adjacent thereto. By this configuration, impingement of ultraviolet light upon the otherwise-obstructed adjacent exterior surfaces is facilitated.

Although previously specified was a garment hanger having a garment support frame carrying a second UV-emitter set with as few as a single UV-emitter, another version prescribes that the second UV-emitter set include at least one UV-emitter disposed along each of the left-side and right-side hanger arms. A still-additional version calls for the second UV-emitter set to include a plurality of UV-emitters disposed along each of the left-side and right-side hanger arms. In general, the greater the number of UV-emitter included within the second UV-emitter set, the more thorough and efficient will be the sterilization of torso-portion and sleeve-portion interior surfaces of a sleeved garment undergoing sterilization. Additionally, a variation of the hanger is configured such that least the shoulder-support and sleeve-support portions of each hanger arm comprises a material that is translucent relative to ultraviolet light. It will be readily appreciated that translucency of the garment support frame facilitates maximizing the surface area of the torso-portion and sleeve-portion interior surfaces that are impinged upon by ultraviolet light emitted from UV-emitters of the second UV-emitter set.

As garment pockets host a particularly high concentration of bacteria, variations of the UV-sterilization include pocket-sterilizing orbs. An illustrative pocket-sterilizing orb includes a bulbous orb housing defining an interior orb cavity containing a third UV-emitter set including at least one electrically energizable UV-emitter. The orb housing is configured for insertion into a pocket of a garment to be sterilized. Moreover, the orb housing comprising a material that is translucent relative to ultraviolet light in order to facilitate maximization of the surface area of the pocket interior surface that is impinged upon by ultraviolet light emitted from the at least one UV-emitter of the third UV-emitter set.

It is generally envisioned that a pocket-sterilizing orb will be inserted into a garment pocket of a garment to be sterilized within the garment enclosure in order to sterilize the pocket interior contemporaneously the sterilization of other garment portions by other elements of the UV-sterilization system. Accordingly, in at least one embodiment, the third UV-emitter set is selectively energizable through an electrically-conductive orb tether having an orb-tether first end electrically connected to the third UV-emitter set and an orb-tether second end that is electrically connectable to an orb-energizing electrical connection situated on at least one of (i) the garment hanger and (ii) one of the housing-wall inside surfaces. In this way, if the first, second, and third UV-emitter sets are electrically linked to a single energizing circuit, they can be activated and deactivated simultaneously.

Representative embodiments are more completely described and depicted in the following detailed description and the accompanying drawings.

PREFERRED EMBODIMENTS

Embodiment 1

A ultraviolet (UV) sterilization system for sterilizing a garment having shoulder, torso, and sleeve portions comprising:
a garment enclosure;
a garment hanger; and
at least three UV emitter sets,
wherein the garment enclosure comprises a housing and a door that are affixed to each other to provide an interior cavity of the garment enclosure,
wherein the housing further comprises a plurality of housing walls that encapsulate the housing, and
wherein each of the plurality of housing walls comprises a housing-wall inside surface located within the plurality of housing walls and a housing-wall outside surface located outside the plurality of housing walls.

Embodiment 2

The UV sterilization system of embodiment 1, wherein the internal cavity is accessed by the door that is attached to the plurality of housing walls so that when the door is closed, the garment enclosure is closed from external access.

Embodiment 3

The UV sterilization system of embodiment 1, wherein the internal cavity is configured to selectively receive and contain the garment to be sterilized.

Embodiment 4

The UV sterilization system of embodiment 1, wherein the housing-wall inside surface comprises a first UV emitter set that is configured to selectively emit UV light when energized by an electrical current.

Embodiment 5

The UV sterilization system of embodiment 1, wherein the first UV emitter set comprises at least one UV emitter that is removably attached to the housing-wall inside surface.

Embodiment 6

The UV sterilization system of embodiment 5, wherein the at least one UV emitter is connected to an external battery source outside the garment enclosure by an electronic wire.

Embodiment 7

The UV sterilization system of embodiment 5, wherein the at least one UV emitter comprises an internal battery that self-powers the UV emitter for emitting UV light.

Embodiment 8

The UV sterilization system of embodiment 5, wherein the housing wall comprises a UV reflective material to reflect UV light emitted from the at least one UV emitter, thereby resulting in an even distribution of the UV light in the interior cavity.

Embodiment 9

The UV sterilization system of embodiment 1, wherein the garment enclosure comprises at least one hanger station that is affixed at or near a top portion of the garment enclosure and further configured to receive the garment hanger.

Embodiment 10

The UV sterilization system of embodiment 9, wherein the garment hanger comprises:
a hook portion; and
a garment-support frame attached to the hook portion,
wherein the hook portion is removably hung on the at least one hanger station as to hold the hanger in place within the garment enclosure.

Embodiment 11

The UV sterilization system of embodiment 10, wherein the garment-support frame comprises:
a left-side hanger arm that corresponds to a left sleeve portion of the garment; and
a right-side hanger arm that corresponds to a right sleeve portion of the garment.

Embodiment 12

The UV sterilization system of embodiment 11, wherein each of the left-side and right-side hanger arms comprises a shoulder-support portion and a corresponding sleeve-support portion configured to support, respectively, the shoulder and sleeve portions of the garment, the sleeve support portion being more distant from the hook portion than is the corresponding shoulder-support portion.

Embodiment 13

The UV sterilization system of embodiment 12, wherein the garment-support frame comprises:
a second UV emitter set,
wherein the second UV emitter set comprises at least one electrically energizable UV-emitter that is configured to emit a UV light upon activation, and
wherein the second UV emitter set is disposed along each of the left-side and right-side hanger arms.

Embodiment 14

The UV sterilization system of embodiment 13, wherein each of the left-side and right-side hanger arms comprise elbow that protrudes outwardly from the left-side and right-side hanger arms to form an obtuse angle between the shoulder-support and sleeve-support portions, such that the sleeve portion of the garment hanging on the garment hanger protrudes at least one of (i) forwardly, and (ii) backwardly from the torso portion of the garment, such that the garment is stretched for maximum exposure to the UV light from the second UV emitter set.

Embodiment 15

The UV sterilization system of embodiment 13, wherein the garment-support frame comprises a material that is translucent relative to UV light as to maximize the garment's exposure to the UV light from the second UV emitter set.

Embodiment 16

The UV sterilization system of embodiment 13, wherein the hanger station comprises a station electrical contact, and wherein the hook portion comprises the hanger electrical contact, such that when the hook is affixed to or hung on the hanger station, the station electrical contact is in electrical contact with the hanger electrical contact as to activate the second UV emitter set.

Embodiment 17

The UV sterilization system of embodiment 16, wherein the station electrical contact is connected to an external energy source.

Embodiment 18

The UV sterilization system of embodiment 1,
wherein the at least three emitter sets comprise a third emitter set,
wherein the third emitter set is configured to be used in an interior surface of the garment,
wherein the third emitter set comprises at least one pocket-sterilizing orb to be inserted in the interior surfaces of the garment,
wherein the at least one pocket-sterilizing orb comprises:
a bulbous orb housing defining an interior orb cavity,
at least one electrically energizable UV-emitter,
an electrically-conductive orb tether with a first and a second end,
wherein the first end connects to the at least one electrically energizable UV-emitter,
wherein the second end connects to an electricity source located on the at least one of: the garment hanger and the housing-wall inside surface, and
wherein the bulbous orb housing comprises a material that is translucent relative to UV light in order to facilitate maximization of the surface area of the interior surface that is impinged upon by a UV light emitted from the at least one electrically energizable UV-emitter of the third UV emitter set.

Embodiment 19

The UV sterilization system of embodiment 1, wherein each of the at least three UV emitter sets are connected to each other and an external power source via an electric wire.

Embodiment 20

A UV sterilization monitoring system comprising:
a data-processing system;
a garment enclosure banks containing on-site machine-to-human interface;
at least one remote machine-to-human interface; and
an individual-user machine-to-human interface,
wherein the data-processing system, the garment enclosure banks, the at least one remote machine-to-human interface, and the individual-user machine-to-human interface are connected to each other via communications network,
wherein the garment enclosure banks comprise housing and a set of UV emitters inside the housing to carry out UV sterilization of a garment once the garment is placed inside the housing; and
wherein the data processing system comprises:
a server,
a database, and
a locker-user data file,
wherein the server, the database, and the locker-user data file are connected via communications network, and
wherein the UV-sterilization monitoring system further comprises a non-transitory machine readable medium having instructions stored thereon and configured when executed to cause the UV sterilization of the garment inside the garment enclosure banks to be carried out based on the locker-user data file.

DETAILED DESCRIPTION OF THE PRESENT DISCLOSURE

Figure 1:
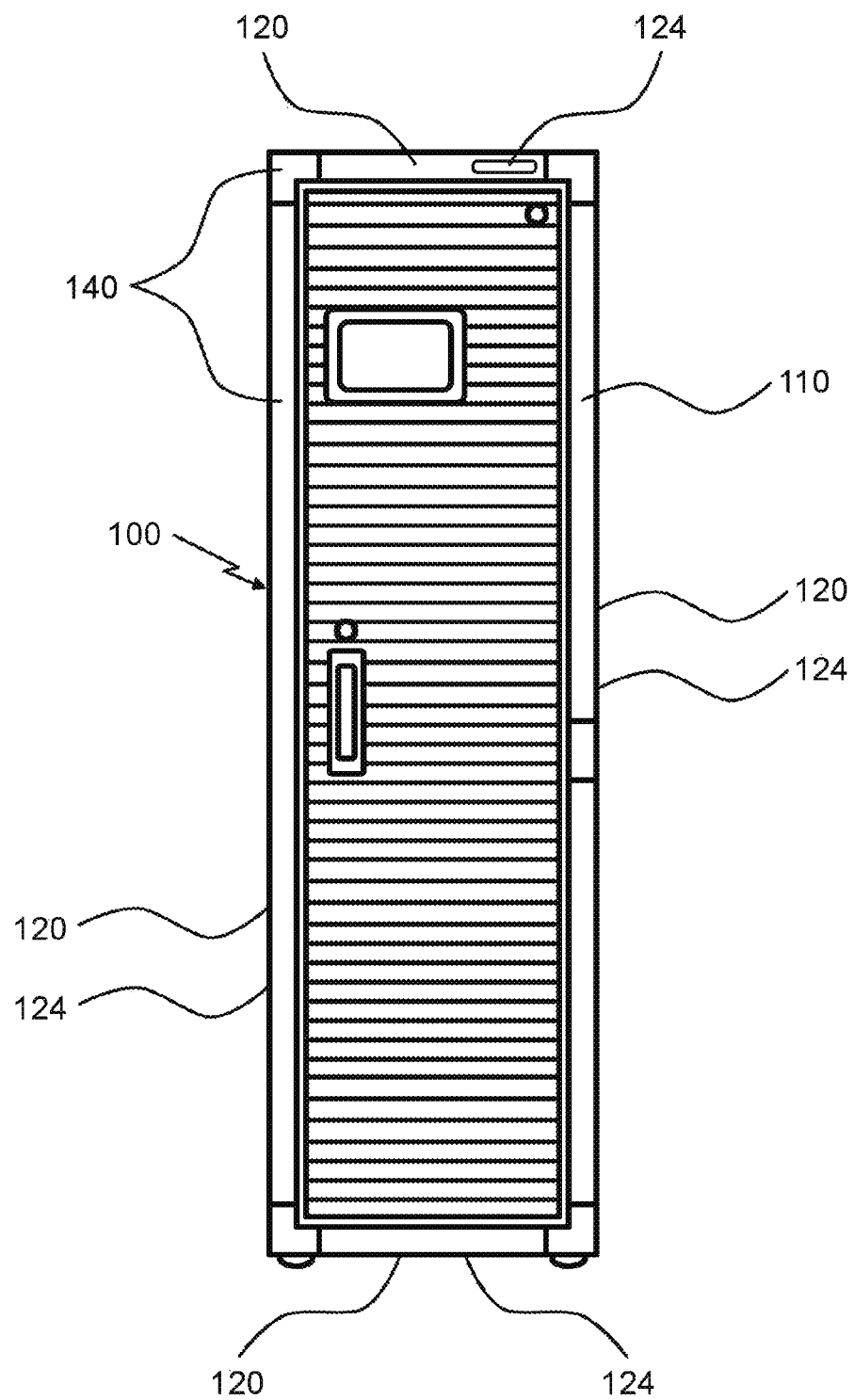
FIG. 1 illustrates a front view of an example of a garment enclosure with a door in the closed position that is constructed in accordance with the principles of the present disclosure.

The following description of variously embodied apparatus and systems for UV-sterilization of garments is demonstrative in nature and is not intended to limit the invention or its application of uses. Accordingly, the various implementations, aspects, versions and embodiments described in the summary and detailed description are in the nature of non-limiting examples falling within the scope of the appended claims and do not serve to restrict the maximum scope of the claims.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one implementation," as used herein does not necessarily refer to the same implementation.

The term "coupled" means at least either a direct electrical connection between the connected items or an indirect connection through one or more passive or active intermediary devices. The term "circuit" means at least either a single component or a multiplicity of components, either active and/or passive, that are coupled together to provide a desired function. The term "signal" as used herein may include any meanings as may be understood by those of ordinary skill in the art, including at least an electric or magnetic representation of current, voltage, charge, temperature, data or a state of one or more memory locations as expressed on one or more transmission mediums, and generally capable of being transmitted, received, stored, compared, combined or otherwise manipulated in any equivalent manner.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a cloud, a super computer, a personal computer, a laptop computer, a palmtop computer, a mobile device, a tablet computer, a notebook computer, a desktop computer, a workstation computer, a server, or the like, or an array of processors, microprocessors, central processing units, general purpose computers, super computers, personal computers, laptop computers, palmtop computers, mobile devices, tablet computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communications network," as used in this disclosure, means a wired and/or wireless medium that conveys data or information between at least two points. The wired or wireless medium may include, for example, a metallic conductor link, a radio frequency (RF) communication link, an Infrared (IR) communication link, telecommunications networks, an optical communication link, internet (wireless and wired) or the like, without limitation. The RF communication link may include, for example, WiFi, WiMAX, IEEE 802.11, DECT, 0G, 1G, 2G, 3G, 4G, 5G or future cellular standards, Bluetooth, Bluetooth Low Energy, NFC, ultrasound, induction, laser (or similar optical transmission) and the like.

A "computer-readable storage medium" or "machine readable medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks, flash memory, and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium or machine readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, the cloud network, or the like, or any combination of the foregoing, any of which may be configured to communicate data via a wireless and/or a wired communication medium. These networks may run a variety of protocols not limited to TCP/IP, IRC, SSL, TLS, UDP, or HTTP.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices, which are not explicitly described as having such functionality or features.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Referring to FIGS. 1-5 concurrently, components of an illustrative UV-sterilization system are shown and described. As indicated in the summary, an illustrative UV-sterilization system includes up to three main cooperating elements, each of which may incorporate UV-emitting elements: (i) a garment enclosure 100, (ii) a garment hanger 200, and (iii) a set of pocket-sterilizing orbs 300. Each of these three elements is the subject of detailed discussion below and in conjunction with referenced drawings.

Figure 2:
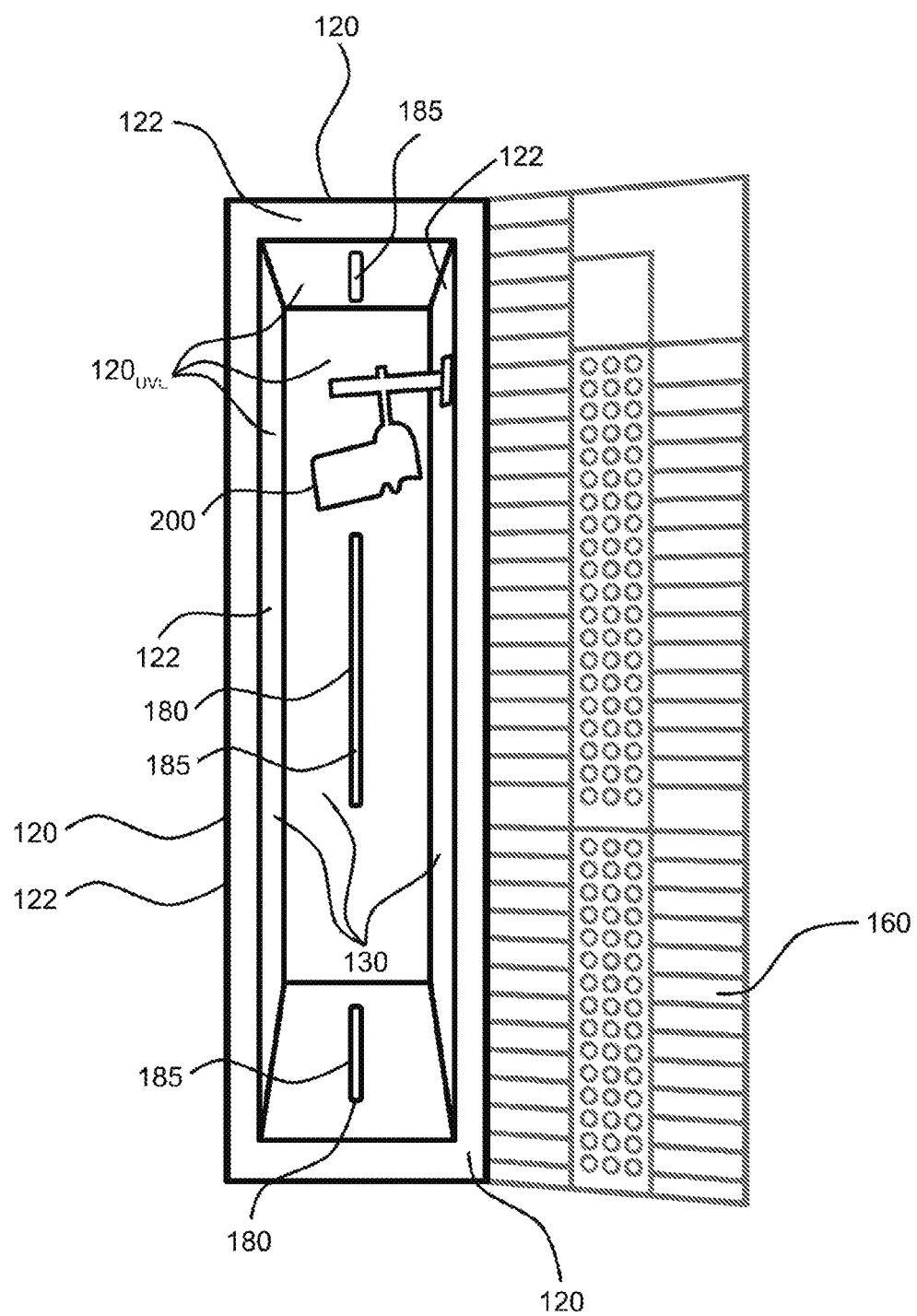
FIG. 2 illustrates a front view of the garment enclosure with the door in an open position that is constructed in accordance with the principles of the present disclosure.

Referring to FIGS. 1 and 2 concurrently, a garment enclosure 100 includes a housing 110 and a door 160 attached to the housing. The housing 110 may include a generally rectangular configuration resembling a standard cabinet, closet, or locker. The housing 110 includes a plurality of housing walls 120, each of which further includes a housing-wall inside surface 122 and a housing-wall outside surface 124. Collectively, the housing-wall inside and outside surfaces 122 and 124 define, respectively, an interior garment cavity 130 and the overall housing exterior 140.

The garment cavity 130 is configured to selectively receive and contain at least one garment to be sterilized. Access to the interior garment cavity 130 is facilitated through a door 160 that is selectively openable, as in FIG. 2, for the introduction into and removal of garments from the garment cavity 130, and closable, as shown in, e.g., FIG. 1, to prevent leakage to the housing exterior of UV light during sterilization cycles.

Disposed on at least one housing-wall inside surface 122 is a first UV-emitter set 180, which includes at least one UV-emitter 185, configured to selectively emit light within the UV range of the electromagnetic spectrum when energized by an electrical current. In one embodiment of the present disclosure, the light emitted may include, e.g., x-rays, gamma rays, infrared, and any other electromagnetic ray.

As shown in, e.g., FIGS. 1-2, it is advantageous for the housing interior (the garment cavity 130) to have disposed along the interior at least one housing-wall inside surface$_{UVL}$ a plurality of UV-emitters 185 configured and mutually arranged to thoroughly bombard the garment cavity 130 with UV light. Moreover, as shown in FIG. 2, for example, thorough and even distribution of UV light is facilitated by rendering the at least one housing-wall inside surfaces 122 reflective of UV light. In an embodiment of the present disclosure, the housing-wall inside surfaces 122 may include a UV-reflective lining 122$_{UVL}$.

The UV-sterilization system incorporate a specially-configured garment hanger 200 that works in conjunction with the garment enclosure 100 with the goal of maximizing the surface area of garment that is impinged upon by sterilizing ultraviolet light. Moreover, as shown in, e.g., FIGS. 3 and 4, the configuration and use of the illustrative garment hanger 200 is shown relative to the hanging of a garment 500 including at least a torso portion 510 with a torso-portion interior surface 512 and a torso-portion exterior surface 514, respectively, and left and right sleeve portions $520_L$ and $520_R$, respectively, depending from the torso portion 510, the sleeve portions $520_L$ and $520_8$ including sleeve-portion interior and exterior surfaces 530 and 540, respectively. Furthermore, in order to demonstrate additional features associated with various versions of the UV-sterilization system, the garment 500 may include a pocket 550.

Figure 4:
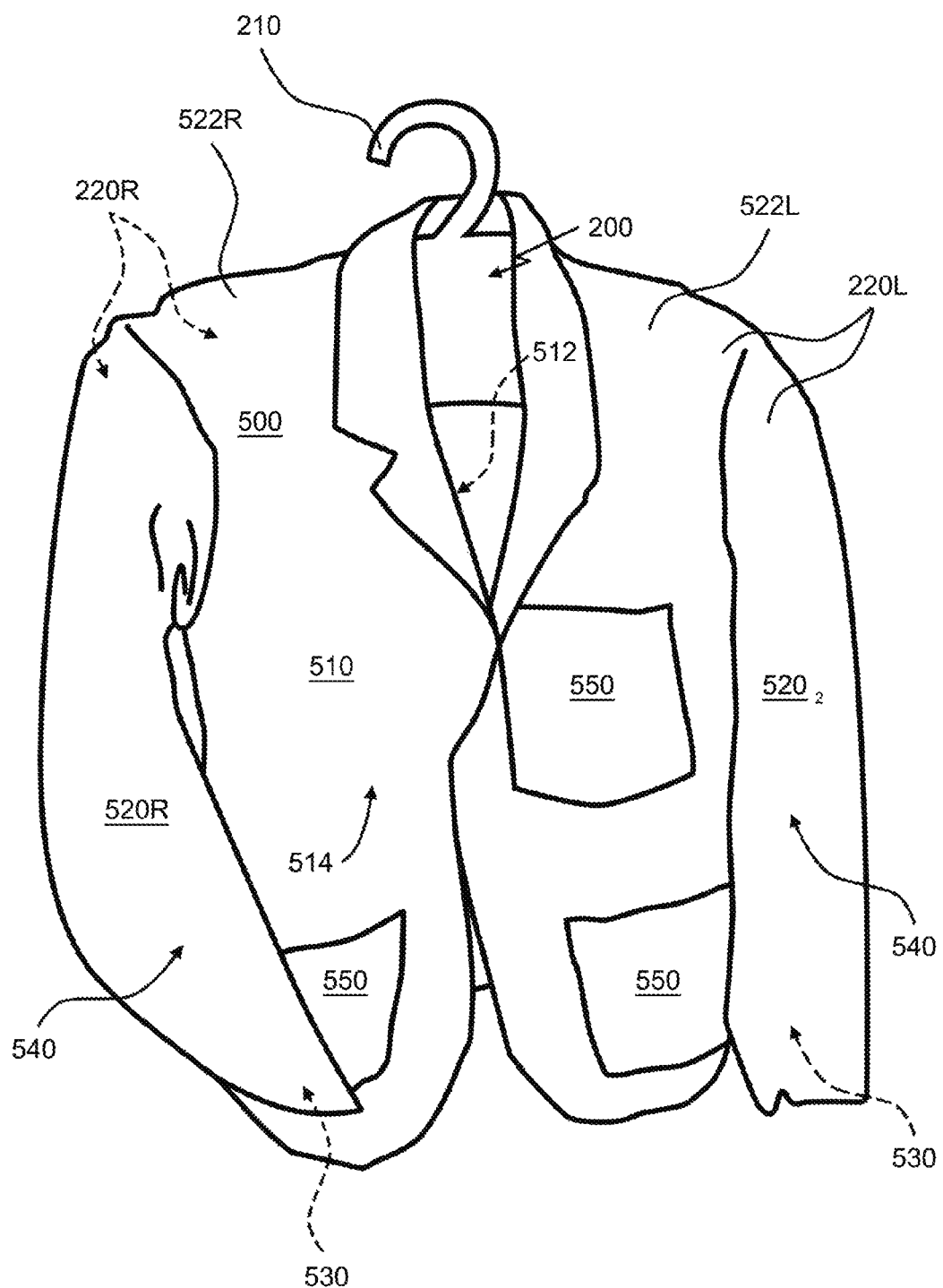
FIG. 4 illustrates a front view of the garment hanger of FIG. 3 with a sleeved garment including pockets hanging thereon in accordance with the principles of the present disclosure.

An illustrative garment hanger 200 may include a hook portion 210 by which the garment hanger 200 may be hung within the garment enclosure 100. Depending from the hook portion 210 is a garment-support frame 215 which further includes a left-side hanger arm $220_L$ and a right-side hanger arm $220_R$ corresponding to, and configured to at least partially coextend with and support, respectively, the left sleeve portion $520_L$ and the right sleeve portions $520_R$ of the garment 500, as shown in FIG. 4. The left-side and right-side hanger arms $220_L$ and $220_R$ comprise, respectively, shoulder-support portions $222_L$ and $222_R$ and corresponding sleeve-support portions $224_L$ and $224_R$ configured to support, respectively, left and right shoulder portions $522_L$ and $522_R$ and the left and right sleeve portions $520_L$ and $520_8$ of the garment 500. The garment-support frame 215 may further include a hook portion 210, upper side 217 and an underside 216.

In order to promote impingement of ultraviolet light upon maximum surface areas of the torso-portion exterior surfaces 514 and the sleeve-portion exterior surfaces 540, each of the left-side hanger arm $220_L$ and right-side hanger arm $220_R$ further includes an elbow 225 defining a "sharp" or "abrupt" elbow angle θ between the corresponding shoulder-support portions $222_L$ and $222_R$ and sleeve-support portions $224_L$ and $224_R$ thereof. The elbows 225 are such that the left and right sleeve portions $520_L$ and $520_R$ of a garment 500 hanging on the garment hanger 200 protrude one of (i) forwardly and (ii) backwardly from the torso portion 510 of the garment 500. Of course, whether the sleeve portions $520_L$ and $520_8$ extend forwardly or backwardly of the torso portion 510 is a function of which way the garment 500 is draped over the garment hanger 200. In the applicable figures, the sleeve portions $520_L$ and $520_R$ extend forwardly of the torso portion 510. It will be appreciated that the sharply-bent configuration of each of the hanger arms $220_L$ and $220_R$ helps maximize the surface area along each sleeve-portion exterior surface 540 that is supported out of contact with the torso-portion exterior surface 514 adjacent thereto. By this configuration, impingement of ultraviolet light emitted from UV-emitters 185 of the first UV-emitter set 180 upon the otherwise-obstructed adjacent exterior surfaces 514 and 540 is facilitated.

Figure 5:
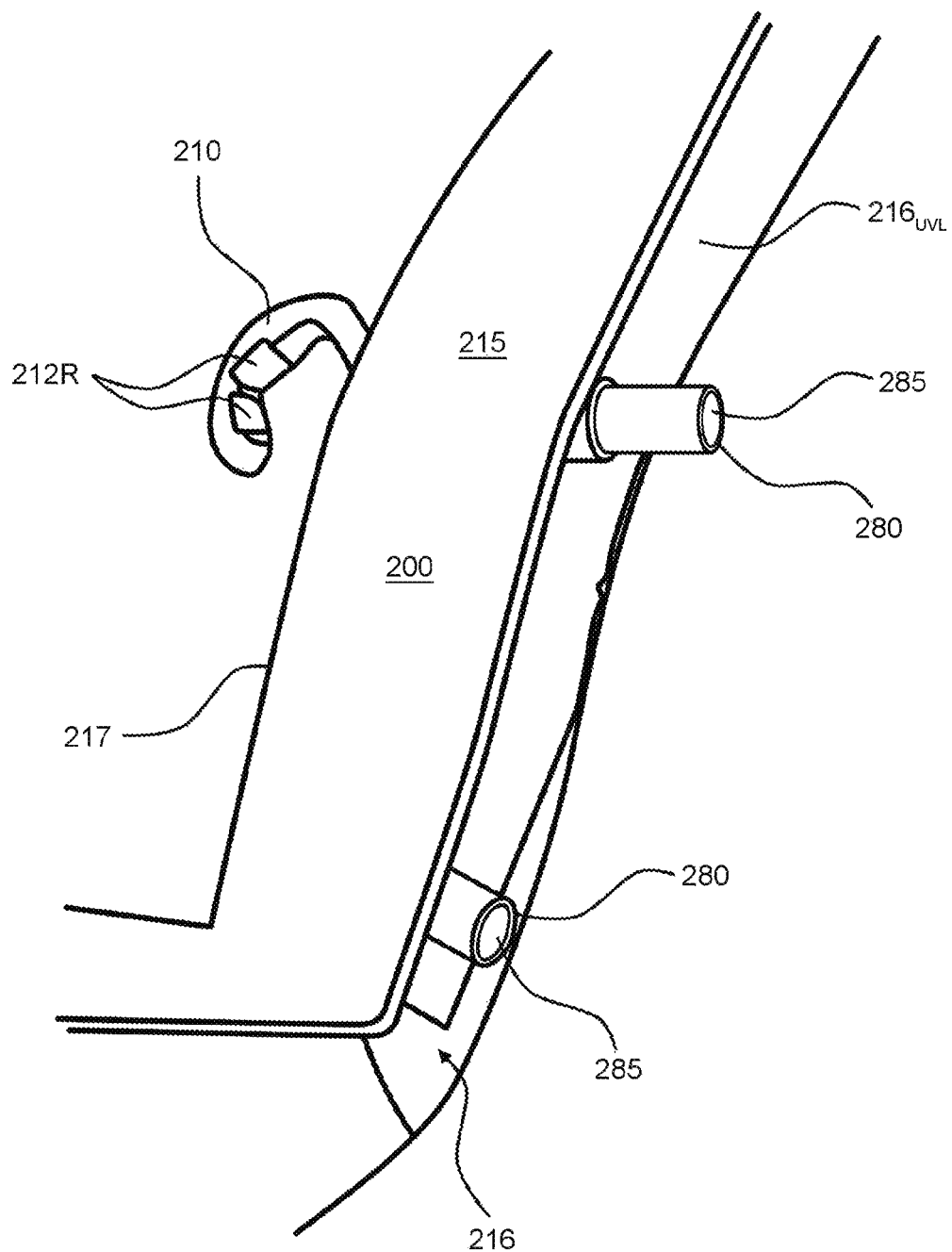
FIG. 5 illustrates a partial view of the garment hanger of FIGS. 3 and 4 showing UV-emitters depending from an underside thereof in accordance with the principles of the present disclosure.

In order to facilitate UV-sterilization of the torso-portion interior surface 512 and sleeve-portion interior surface 530, a garment hanger 200 is configured to incorporate a second UV-emitter set 280. The second UV-emitter set 280 includes at least one electrically energizable UV-emitter 285. In the view of FIG. 5, UV-emitters 285 of the second UV-emitter set 280 may be carried by or attached to the garment-support frame 215. The UV-emitters 285 may be distributed along an underside 216 of an opaque garment-support frame 215. However, it is to be understood that this arrangement, as well as the opacity of the garment-support frame 215 are illustrative and non-limiting in nature. For instance, in another embodiment of the present disclosure, the garment-support frame 215 may be constructed, at least in part or in its entirety, from a material that is translucent with respect to ultraviolet light in order to promote the impingement of ultraviolet light upon the torso-portion interior surface 512 and sleeve-portion interior surfaces 530 resting upon the upper side 217 of the garment-support frame 215. Returning to the opaque version depicted in, e.g., FIG. 5, the underside 216 of the opaque garment-support frame 215 may be lined with a UV-reflective lining $216_{UVL}$. The UV-reflective lining $216_{UVL}$ reflects ultraviolet light emitted from UV-emitters 285 of the second UV-emitter set 280 downwardly and into the lower portions of the torso-portion interior surface 512 and sleeve-portion interior surface 530. It should, of course, be noted that another version of the garment hanger 200 within the scope and contemplation of the invention may include a garment-support frame 215 that is both translucent to ultraviolet light and includes a UV-reflective lining $216_{UVL}$.

Figure 3:
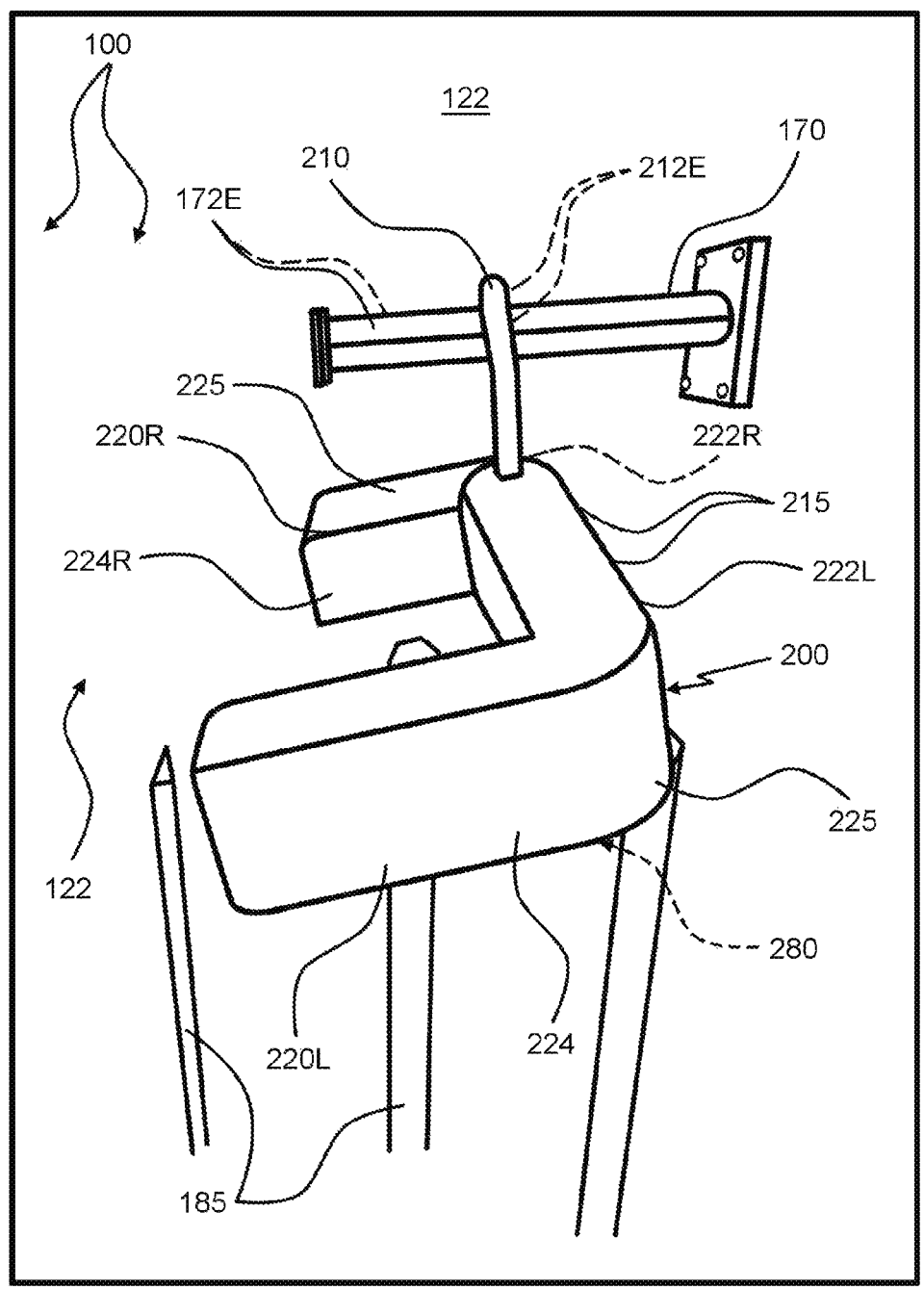
FIG. 3 illustrates a left side view of garment hanger for use in conjunction with the garment enclosure of FIGS. 1 and 2.

The second UV-emitter set 280 carried by the garment hanger 200 requires a source of electrical power available to selectively energize its constituent UV-emitters 285. To this end, means of supplying electrical current to the second UV-emitter set 280 are discussed with principal reference to, e.g., FIGS. 3 and 5. As seen in FIG. 3, a hanger station 170 is provided within the garment enclosure 100 and configured to receive for hanging the hook portion 210 of the garment hanger 200. The presence of the hook portion 210 upon the hanger station 170 defines a detectable registration condition. In the version of the hanger station 170 and garment hanger 200 depicted, the garment hanger 200 being "in registration" with the hanger station 170 enables or triggers selective energizing of the second UV-emitter set 280. More specifically, the hanger station 170 may be provided with station electrical contacts 172e and the hook portion 210 of the garment hanger 200 is provided with hanger electrical contacts 212e. When the hook portion 210 is properly seated upon the hanger station 170, the hanger electrical contacts 212e are in electrical contact with the station electrical contacts 172e, thereby establishing electrical connectivity between the second UV-emitter set 280 and a power source (not shown) that, for example, provides electrical power to the garment enclosure 100 as whole (e.g., to the first UV-emitter set 180 disposed within the housing interior of the garment enclosure 100).

Figure 6:
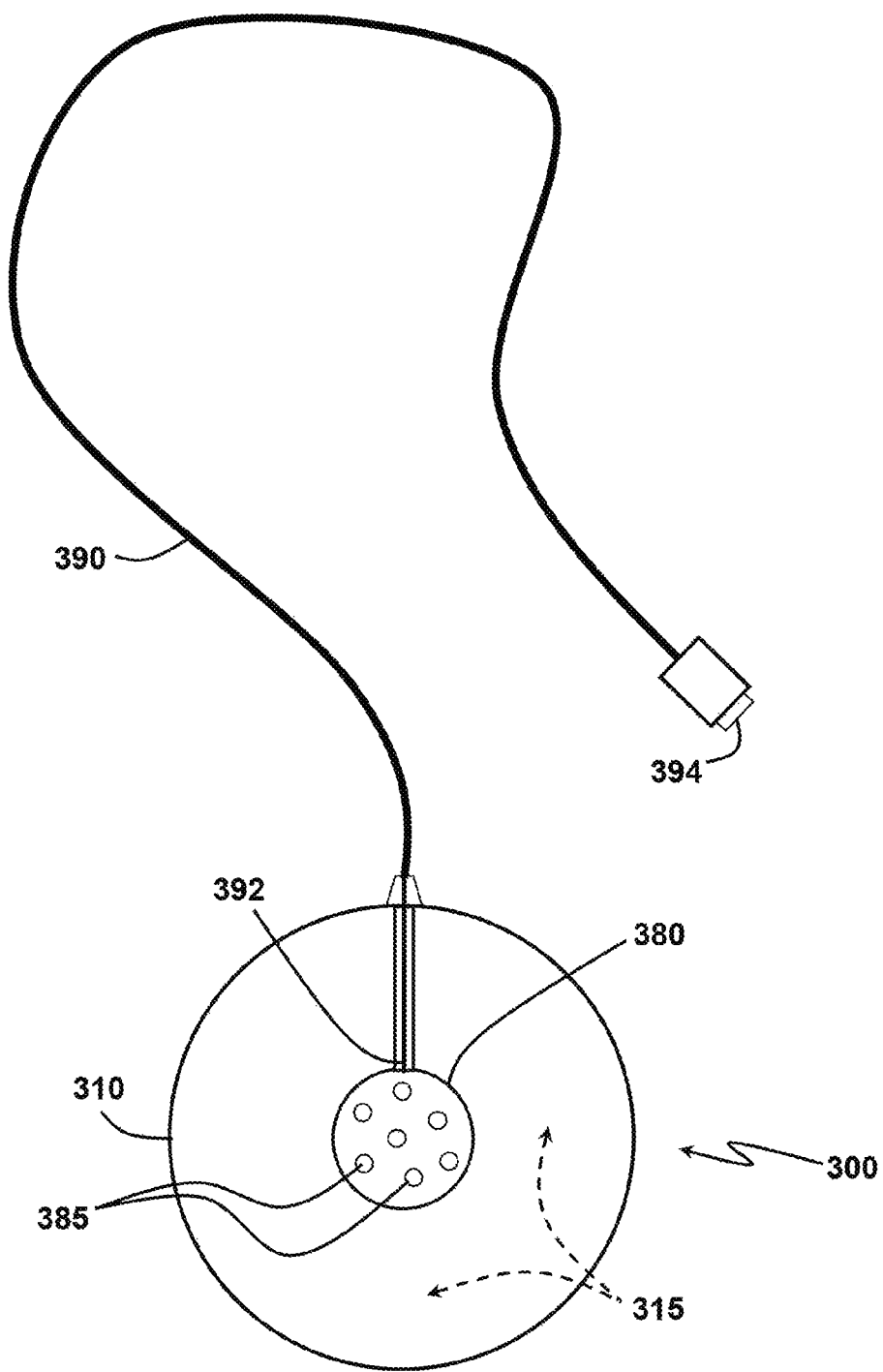
FIG. 6 illustrates an example of a pocket-sterilizing orb that is constructed in accordance with the principles of the present disclosure.

The UV-sterilization system further includes pocket-sterilizing orbs 300. As shown in, e.g., FIG. 6, the pocket-sterilizing orb 300 may include a bulbous orb housing 310 defining an interior orb cavity 315, a third UV-emitter set 380 placed within the interior orb cavity 315 and containing at least one electrically energizable UV-emitter 385, and an orb-tether first end 392, an orb-tether second end 394, and an electrically-conductive orb tether 390, wherein the orb-tether first end 392 is connected to the third UV-emitter set 380, wherein the orb-tether first end 392 is connected to the orb-tether second end 394 via the electrically-conductive orb tether 390. The orb housing 310 may be configured for insertion into a pocket 550 of a garment 500 to be sterilized. Additionally, the orb housing 310 is fabricated from a material that is translucent relative to the UV light in order to facilitate maximization of the surface area of the pocket interior surface that is impinged upon by ultraviolet light emitted from the at least one UV-emitter 385 of the third UV-emitter set 380.

The pocket-sterilizing orb may be inserted into a garment pocket 550 of a garment 500 to be sterilized within the garment enclosure 100 in order to sterilize the pocket interior surface while simultaneously sterilizing other garment portions by other elements of the UV-sterilization system. Accordingly, in at least one version, the third UV-emitter set 380 is selectively energizable through the electrically-conductive orb tether 390 having the orb-tether first end 392 electrically connected to the third UV-emitter set 380 and the orb-tether second end 394 that is electrically connectable to an orb-energizing electrical connection situated on at least one of (i) the garment hanger 200 and (ii) one of the housing-wall inside surfaces (electrical connection not shown in this provisional, but readily comprehensible and therefore adequately disclosed). In this way, if the first, second, and third UV-emitter sets 180, 280, and 380, respectively, are electrically linked to a single energizing circuit, they can be activated and deactivated simultaneously. In an embodiment, this activation and deactivation may be configured to be carried out by a manual input or instruction by a user, or automatically upon detection of the presence (or absence) of the garment 500 inside the garment enclosure 100.

Figure 7:
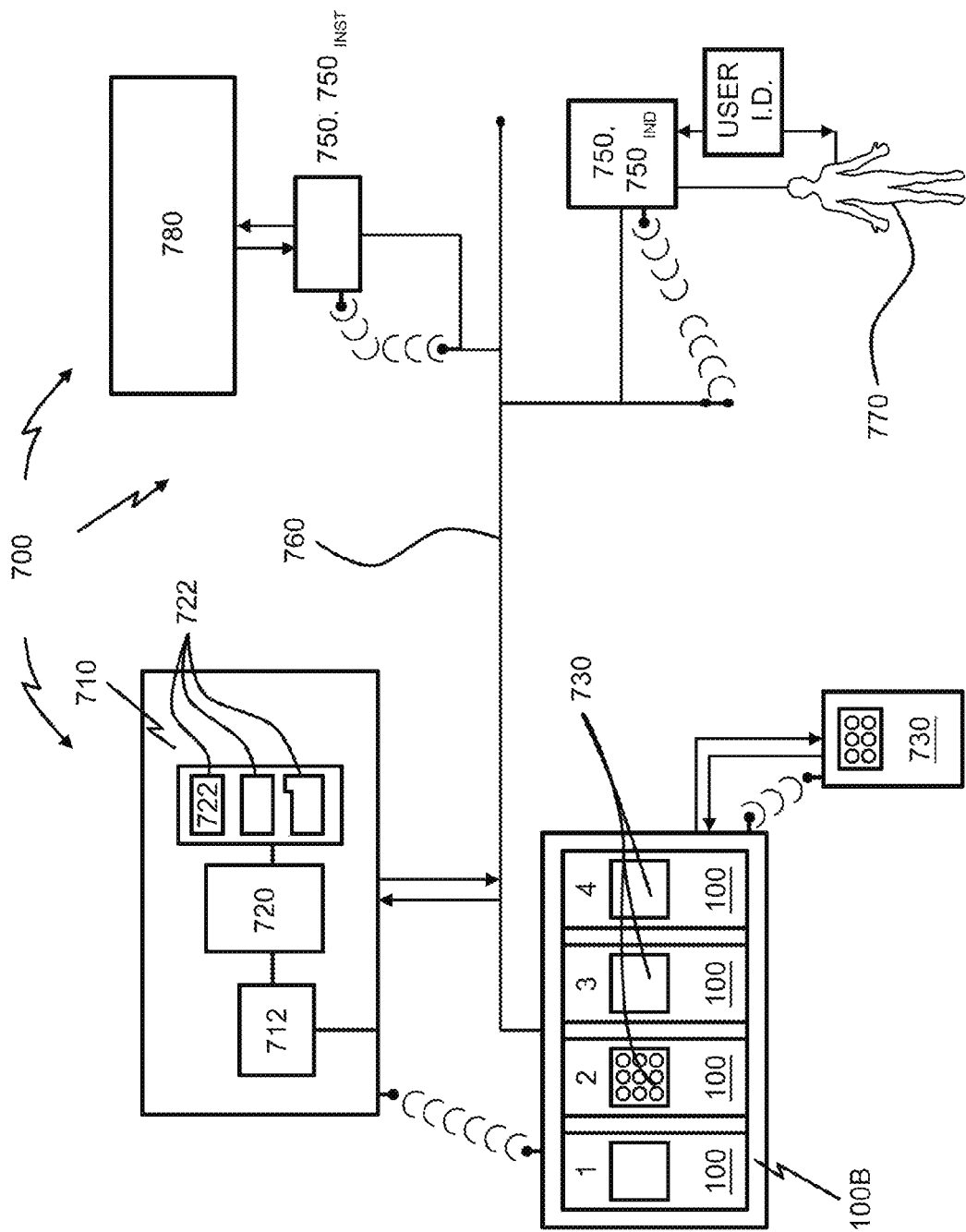
FIG. 7 illustrates an example of a communications and data-processing architecture for the implementation of a method and a system for remotely monitoring the status of the UV-sterilization garment enclosure in accordance with the principles of the present disclosure.

In order to encourage and monitor usage, particularly in institutional settings, each of various embodiments of a UV-sterilization system is cooperatively associated with a method and system for remotely status-monitoring UV-sterilization garment enclosures 100. FIG. 7 illustrates an example of an implementation and associated architecture for status-monitoring a UV-sterilization system as disclosed herein. For ease of reference and discussion, implementations of the monitoring system and associated architecture are hereinafter referred to as "UV-sterilization monitoring system 700."

The UV-sterilization monitoring system 700 may include data-processing system 710, garment enclosure banks 100B containing on-site machine-to-human interface 730, at least one remote machine-to-human interface 750, and an individual-user machine-to-human interface 750$_{IND}$, wherein each of the aforementioned elements may be connected to each other via communications network.

The data processing system 710 may include a computer 712, a computer memory 720, and a locker-user data file 722, wherein the computer 712, the computer memory 720, and the locker-user data file 722 are connected via communications network. Each of the computer 712, the computer memory 720, and the locker-user data file 722 may include a server and a database, wherein each of the server and the database may further include a machine readable medium that is configured to carry out the processes for sanitizing a garment as disclosed herein. Although the UV-sterilization monitoring system 700 may be implemented in association with as few as one UV-sterilization garment enclosure 100, such a system 700 may also be associated or connected with a plurality or "bank" of garment enclosures 100 via communications network. Accordingly, the UV-sterilization monitoring system 700 provides an example of a garment enclosure bank 100B illustratively including more than one garment enclosures 100, According to an embodiment of the present disclosure, there is associated with each garment enclosure 100 an on-site machine-to-human interface 730. In another embodiment, each garment enclosure 100 includes a dedicated machine-to-human interface 730, while, in another version, a single machine-to-human interface 730 is communicatively linked to each of several garment enclosures 100. For purposes of efficiency and brevity in explanation, both options are shown in coexistence in the schematic of FIG. 7. In either or both cases, an on-site machine-to-human interface 730 may be configured as a keypad and/or touchscreen with an associated display. The on-site machine-to-human interface 730 may further include a kiosk or another computer that is capable of interacting with the user via, e.g., receiving an input, relaying information, and the like.

In each of various implementations, the data processing system 710 may be communicatively linked (via, e.g., communications network) and associated with is the at least one remote machine-to-human interface 750. In a first instance, an individual-user machine-to-human interface 750$_{IND}$ enables a human individual user(s) to communicate remotely with any of the components of the UV-sterilization monitoring system 700 for any of various purposes. For instance, an individual user who has placed a garment 500 in a garment enclosure 100 for sterilization may wish to check on the status of a cleaning cycle so that he or she knows when the garment 500 is clean. For this purpose, it is also contemplated that the UV-sterilization monitoring system 700 could send a notification to a user's individual-user machine-to-human interface 750$_{IND}$ when a cleaning cycle is complete. The user's individual-user machine-to-human interface 750$_{IND}$ may include, e.g., a computer. Alternatively, a user seeking an available garment enclosure 100 in which to place a garment 500 requiring cleaning could consult the UV-sterilization monitoring system 700 through his or her individual-user machine-to-human interface 750$_{IND}$ to locate a nearest available garment enclosure 100.

Alternatively (or additionally) to associated individual-user machine-to-human interfaces 750$_{IND}$, the UV-sterilization monitoring system 700 may include at least one institutional-user machine-to-human interface 750$_{INST}$ that is communicatively linked (via, e.g., communications network) and associated with the data processing system 710. In this context, "institutional-user" may include a supervisor, a system operator, an authorized user, or an organization having an interest in monitoring use of garment enclosures 100 associated with the UV-sterilization monitoring system 700 by individuals. Such institutional-user may include, by way of non-limiting example, hospitals, nursing homes, restaurants, hotels, department stores wear clothes are tried on by customers, and sports, recreation, and exercise facilities.

The UV-sterilization monitoring system 700 is especially useful in a hospital where hospital administrators and staff have a vested institutional interest in maintaining as clean and sterile an environment as possible. It follows that a hospital would benefit from additional ways to encourage and monitor the extent to which individual medical professionals and students observe cleanliness protocols. Accordingly, illustratively implemented, individual users may be uniquely identified to the UV-sterilization monitoring system 700 and the locker-user data file 722 may be associated in the computer memory 720 with each such user individually. Each time the locker user interacts with the UV-sterilization monitoring system 700, he or she may actively or passively identifies himself or herself to the system 700 by, for example, use of a key-entered identification number, a scanned code such as a barcode, username and password, and/or an IP address associated with a device serving as his or her individual-user machine-to-human interfaces 750$_{IND}$. Maintained in the locker-user data file 722 associated with each locker user is information such as, for example, (i) dates and times of use, (ii) duration of use, (iii) location of garment enclosure's 100 used, (iv) types of garments 500 sterilized, and (v) elapsed time since most recent use, by way of non-limiting example.

By maintaining and providing access to individual-user information, an institutional user can track and analyze data files 722 for the purposes of encouraging and rewarding individual use, but can also use this data for more holistic purposes. For instance, if the institutional user such as a hospital has various garment enclosure banks 100B situated throughout its facilities, it can—after sufficient data has been accumulated—optimize locations for the addition or subtraction of garment enclosures 100 associated with particular garment enclosure banks 100B. Also, after initial installation and use of a certain number of garment enclosures 100 arranged in strategic locations, the institutional user could track whether there has been a corresponding reduction in infections, etc. since initial installation and/or situating of garment enclosure banks 100B in specific locations throughout its facilities. Remote machine-to-human interfaces 750, whether they are individual-user machine-to-human interfaces $750_{IND}$ or institutional-user machine-to-human interfaces $750_{INST}$, may include a computer. Additionally, individually, the various remote machine-to-human interfaces 750 may be communicatively linked to the data processing system 710 by communications network as indicated schematically in, e.g., FIG. 7. As shown, hardwiring may be indicated by solid-line connections while wireless communication links are indicated by arcuate wave-front symbols.

The foregoing is considered to be illustrative of the principles of the invention. Furthermore, since modifications and changes to various aspects and implementations will occur to those skilled in the art without departing from the scope and spirit of the invention, it is to be understood that the foregoing does not limit the invention as expressed in the appended claims to the exact constructions, implementations and versions shown and described.

What is claimed is:

1. An ultraviolet (UV) sterilization system for sterilizing a garment having a shoulder portion, a torso portion, and two sleeve portions, the system comprising:
    a garment enclosure;
    a garment hanger; and
    at least three UV emitter sets,
    wherein the garment enclosure comprises a housing and a door that are affixed to each other to provide an interior cavity of the garment enclosure,
    wherein the housing further comprises a plurality of housing walls that encapsulate the housing,
    wherein each of the plurality of housing walls comprises a housing-wall inside surface located within the plurality of housing walls and a housing-wall outside surface located outside the plurality of housing walls,
    wherein the garment hanger includes a hook portion and a garment-support frame depending from the hook portion, the garment-support frame including at least two hanger arms extending from the hook portion, each hanger arm having a shoulder-support portion configured to support one of the shoulder portions of the garment, and a sleeve-support portion configured to support one of the sleeve portions of the garment, the sleeve-support portion of each of the at least two hanger arms protruding (i) downward relative to the shoulder-support portions and (ii) forward or backward relative to the shoulder-support portions,
    wherein the sleeve-support portion of each respective hanger arm of the at least two hanger arms protrudes forward or backward, and protrudes outward at an obtuse angle relative to the shoulder-support portion of the same respective hanger arm, such that the sleeve-support portions of the at least two hanger arms extend outward from the shoulder-support portions at the obtuse angle and away from each other on an identical side of the garment-support frame, and such that the two sleeve portions of the garment are spaced apart from the torso portion of the garment when the garment is supported by the garment hanger,
    wherein the at least three UV emitter sets includes at least one UV-emitter coupled to a bottom surface of the garment-support frame such that the at least two hanger arms are positioned between the (i) the hook portion of the garment hanger and (ii) the at least one UV-emitter, and
    wherein the garment hanger is formed from a material that is opaque to UV light, the garment hanger further including a UV-reflective lining attached to a bottom surface of the garment-support frame such that the at least two hanger arms are positioned between the (i) the hook portion of the garment hanger and (ii) the UV-reflective lining, and such that the UV-reflective lining and the at least one UV-emitter are configured to be disposed inside the garment when the garment is supported by the garment hanger.

2. The UV sterilization system of claim 1, wherein the internal cavity is accessed by the door that is attached to the plurality of housing walls so that when the door is closed, the garment enclosure is closed from external access.

3. The UV sterilization system of claim 1, wherein the internal cavity is configured to selectively receive and contain the garment to be sterilized.

4. The UV sterilization system of claim 1, wherein the housing-wall inside surface comprises a first UV emitter set that is configured to selectively emit UV light when energized by an electrical current.

5. The UV sterilization system of claim 1, wherein the first UV emitter set comprises at least one UV emitter that is removably attached to the housing-wall inside surface.

6. The UV sterilization system of claim 5, wherein the at least one UV emitter is connected to an external battery source outside the garment enclosure by an electronic wire.

7. The UV sterilization system of claim 5, wherein the at least one UV emitter comprises an internal battery that self-powers the UV emitter for emitting UV light.

8. The UV sterilization system of claim 5, wherein the housing wall comprises a UV reflective material to reflect UV light emitted from the at least one UV emitter, thereby resulting in an even distribution of the UV light in the interior cavity.

9. The UV sterilization system of claim 1, wherein the garment enclosure comprises at least one hanger station that is affixed at a top portion of the garment enclosure and further configured to receive the garment hanger.

10. The UV sterilization system of claim 9, wherein the garment hanger includes a hook portion that is removably hung on the at least one hanger station as to hold the hanger in place within the garment enclosure.

11. The UV sterilization system of claim 1, wherein the at least two hanger arms of the garment-support frame include:
    a left-side hanger arm that corresponds to a left sleeve portion of the garment; and
    a right-side hanger arm that corresponds to a right sleeve portion of the garment.

12. The UV sterilization system of claim 1, wherein the garment-support frame comprises:
    a second UV emitter set,
    wherein the second UV emitter set comprises at least one electrically energizable UV-emitter that is configured to emit a UV light upon activation, and
    wherein the second UV emitter set is disposed along each of the at least two hanger arms.

13. The UV sterilization system of claim 12, wherein the hanger station comprises a station electrical contact, and wherein the hook portion comprises the hanger electrical contact, such that when the hook is affixed to or hung on the hanger station, the station electrical contact is in electrical contact with the hanger electrical contact as to activate the second UV emitter set.

14. The UV sterilization system of claim 13, wherein the station electrical contact is connected to a power source that is external to the garment enclosure.

15. The UV sterilization system of claim 1,
wherein the at least three emitter sets comprise a third emitter set,
wherein the third emitter set is configured to be used in an interior surface of the garment, wherein the third emitter set comprises at least one pocket-sterilizing orb to be inserted in the interior surfaces of the garment,
wherein the at least one pocket-sterilizing orb comprises:
a bulbous orb housing defining an interior orb cavity,
at least one electrically energizable UV-emitter,
an electrically-conductive orb tether with a first and a second end, wherein the first end connects to the at least one electrically energizable UV-emitter,
wherein the second end connects to an electricity source located on at least one of: the garment hanger or the housing-wall inside surface, and
wherein the bulbous orb housing comprises a material that is translucent relative to UV light in order to facilitate maximization of the surface area of the interior surface that is impinged upon by a UV light emitted from the at least one electrically energizable UV-emitter of the third UV emitter set.

16. The UV sterilization system of claim 1, wherein each of the at least three UV emitter sets are connected to each other and a power source via an electric wire, the power source being external to the garment enclosure.

17. A UV sterilization monitoring system comprising:
a data-processing system;
a garment enclosure bank containing on-site machine-to-human interface; at least one remote machine-to-human interface; and
an individual-user machine-to-human interface,
wherein the data-processing system, the garment enclosure bank, the at least one remote machine-to-human interface, and the individual-user machine-to-human interface are connected to each other via communications network,
wherein the garment enclosure bank comprise one or more housings and a set of UV emitters inside each of the one or more housings to carry out UV sterilization of a garment once the garment is placed inside each of the one or more housings, and wherein each of the one or more housings includes a garment hanger having a hook portion and a garment-support frame depending from the hook portion, the garment-support frame including at least two hanger arms extending from the hook portion, a sleeve-support portion of each respective hanger arm of the at least two hanger arms protruding forward or backward, and protruding outward, at an obtuse angle relative to shoulder-support portions of the same respective hanger arms, such that the sleeve-support portions of the at least two hanger arms extend outward from the shoulder-support portions at the obtuse angle and away from each other on an identical side of the garment-support frame, and such that sleeve portions of the garment are spaced apart from a torso portion of the garment when the garment is supported by the garment hanger,
wherein the set of UV emitters inside each of the one or more housings includes at least one UV-emitter coupled to a bottom surface of the garment-support frame of the garment hanger of each of the one or more housings such that the at least two hanger arms are positioned between the (i) the hook portion of the garment hanger and (ii) the at least one UV-emitter,
wherein the garment hanger of each of the one or more housings is formed from a material that is opaque to UV light and includes a UV-reflective lining attached to a bottom surface of the garment-support frame, such that the at least two hanger arms are positioned between (i) the hook portion of the garment hanger and (ii) the UV-reflective lining, and such that the UV-reflective lining and the at least one UV-emitter are configured to be disposed inside the garment when the garment is supported by the garment hanger,
wherein the data processing system comprises:
a server,
a database, and
a locker-user data file,
wherein the server, the database, and the locker-user data file are connected via communications network, and wherein the UV-sterilization monitoring system further comprises a non-transitory machine readable medium having instructions stored thereon and configured when executed to cause the UV sterilization of the garment inside the garment enclosure bank to be carried out based on the locker-user data file.

18. The UV sterilization system of claim 1, wherein each of the at least two hanger arms protrudes in a straight line from the garment-support frame at the obtuse angle.

* * * * *